(12) United States Patent
Hamilton et al.

(10) Patent No.: US 12,424,338 B2
(45) Date of Patent: Sep. 23, 2025

(54) TRANSFER LEARNING TECHNIQUES FOR USING PREDICTIVE DIAGNOSIS MACHINE LEARNING MODELS TO GENERATE TELEHEALTH VISIT RECOMMENDATION SCORES

(71) Applicant: UnitedHealth Group Incorporated, Minnetonka, MN (US)

(72) Inventors: Rick A. Hamilton, Charlottesville, VA (US); Garry Choy, Irvine, CA (US); Rafael Campos Do Amaral E Vasconcellos, Plymouth, MN (US); Gregory J. Boss, Saginaw, MI (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 401 days.

(21) Appl. No.: 17/548,969

(22) Filed: Dec. 13, 2021

(65) Prior Publication Data
US 2023/0187085 A1      Jun. 15, 2023

(51) Int. Cl.
| | |
|---|---|
| *G16H 80/00* | (2018.01) |
| *G16H 10/65* | (2018.01) |
| *G16H 50/20* | (2018.01) |

(52) U.S. Cl.
CPC .............. *G16H 80/00* (2018.01); *G16H 10/65* (2018.01); *G16H 50/20* (2018.01)

(58) Field of Classification Search
CPC ........ G16H 80/00; G16H 50/20; G16H 10/65; G16H 10/60; G16H 50/30; G16H 50/70; G06N 3/08; G06N 20/00; G06F 40/205

(Continued)

(56) References Cited

U.S. PATENT DOCUMENTS

| | | |
|---|---|---|
| 5,611,350 A | 3/1997 | John |
| 6,944,536 B2 | 9/2005 | Singleton |

(Continued)

FOREIGN PATENT DOCUMENTS

| | | |
|---|---|---|
| CN | 106778038 A | 5/2017 |
| IN | 201841026405 A | 7/2020 |
| WO | 2019/211845 A1 | 11/2019 |

OTHER PUBLICATIONS

Final Rejection Mailed on Jan. 24, 2024 for U.S. Appl. No. 17/643,030, 36 page(s).

(Continued)

*Primary Examiner* — Alaaeldin M. Elshaer
(74) *Attorney, Agent, or Firm* — Alston & Bird LLP

(57) ABSTRACT

Various embodiments of the present invention provide methods, apparatus, systems, computing devices, computing entities, and/or the like for performing predictive data analysis operations. For example, certain embodiments of the present invention utilize systems, methods, and computer program products that perform predictive data analysis operations by an end-to-end machine learning framework that performs at least the following steps/operations: (i) a service request data object is processed by a diagnosis prediction machine learning model to generate a probabilistic diagnosis data object, (ii) the probabilistic diagnosis data object is processed by the hybrid diagnosis-provider classification machine learning model to generate a variable-length classification for the service request data object, and (iii) the variable-length classification is processed by a telehealth visit recommendation scoring machine learning model to generate a telehealth visit recommendation score for the service request data object.

18 Claims, 8 Drawing Sheets

(58) Field of Classification Search
USPC .......................................................... 705/2, 3
See application file for complete search history.

(56) References Cited

U.S. PATENT DOCUMENTS

| | | | |
|---|---|---|---|
| 9,886,493 | B2 | 2/2018 | Coleman et al. |
| 10,074,059 | B1 | 9/2018 | Albro et al. |
| 10,368,806 | B2 | 8/2019 | Kim |
| 10,572,626 | B2 | 2/2020 | Balram |
| 2009/0198733 | A1 | 8/2009 | Gounares et al. |
| 2010/0312581 | A1 | 12/2010 | Wachtell et al. |
| 2013/0035955 | A1 | 2/2013 | Torres |
| 2013/0224117 | A1* | 8/2013 | Royall .................. G16H 50/50 424/9.2 |
| 2013/0226601 | A1 | 8/2013 | Razmi et al. |
| 2015/0164363 | A1 | 6/2015 | Kocher et al. |
| 2015/0248470 | A1 | 9/2015 | Coleman et al. |
| 2015/0248536 | A1 | 9/2015 | Tawil et al. |
| 2016/0055307 | A1* | 2/2016 | Macoviak ............ G16H 20/10 705/2 |
| 2016/0071171 | A1 | 3/2016 | Cancelliere, III et al. |
| 2017/0098051 | A1* | 4/2017 | Balram ................. G16H 50/20 |
| 2018/0285527 | A1 | 10/2018 | Abadir |
| 2019/0387335 | A1 | 12/2019 | Hughes et al. |
| 2019/0387998 | A1 | 12/2019 | Garten et al. |
| 2020/0015696 | A1 | 1/2020 | Connolly et al. |
| 2020/0066397 | A1 | 2/2020 | Rai et al. |
| 2020/0121544 | A1 | 4/2020 | George et al. |
| 2020/0155061 | A1 | 5/2020 | Pradeep |
| 2020/0210868 | A1 | 7/2020 | Gharat et al. |
| 2020/0215296 | A1 | 7/2020 | Rabin et al. |
| 2020/0222010 | A1 | 7/2020 | Howard |
| 2020/0302825 | A1 | 9/2020 | Sachs et al. |
| 2020/0303045 | A1 | 9/2020 | Harnach |
| 2020/0337625 | A1 | 10/2020 | Aimone et al. |
| 2020/0397534 | A1 | 12/2020 | Farrelly et al. |
| 2020/0411170 | A1 | 12/2020 | Brown et al. |
| 2021/0022638 | A1 | 1/2021 | Holcman et al. |
| 2021/0022688 | A1 | 1/2021 | Lee et al. |
| 2021/0343411 | A1* | 11/2021 | Zhang ................... G06N 5/045 |
| 2021/0345947 | A1 | 11/2021 | McCarthy et al. |
| 2021/0375480 | A1 | 12/2021 | Mahon et al. |
| 2022/0147865 | A1* | 5/2022 | Naidoo ................. G06N 3/044 |
| 2023/0154608 | A1* | 5/2023 | Gunsola ................ G16H 50/30 705/2 |
| 2023/0177369 | A1 | 6/2023 | Hamilton et al. |
| 2023/0178215 | A1 | 6/2023 | Muse et al. |

OTHER PUBLICATIONS

"Emergency Patient Destinations and Hospital Diversion," New York State Department of Health, Bureau of EMS Policy Statement, Jan. 11, 2006, (2 pages), (Article), [Retrieved from the Internet Apr. 8, 2022] <URL: https://www.health.ny.gov/professionals/ems/policy/06-01.htm.

"Investigation of the Interaction Between External Stimulation and Ongoing Brain Activity in Cortical Networks: Analysis, Modeling and Empirical Corroboration," Cordis, European Commission, Apr. 15, 2016, (4 pages), (article), [Retrieved from the Internet Apr. 8, 2022] <URL: https://cordis.europa.eu/article/id/181046-external-stimuli-and-their-effect-on-brain-activity>.

"Online Doctors Available 24/7 Start a Telehealth Visit," Doctor+ on Demand by Included Health, (9 pages), (available online), [Retrieved from the Internet Apr. 8, 2022] <URL: https://doctorondemand.com/>.

Albahri, O.S. et al. "Fault-Tolerant mHealth Framework in the Context of IoT-Based Real-Time Wearable Health Data Sensors," IEEE Access, vol. 7, Apr. 11, 2019, pp. 50052-50080, DOI: 10.1109/ACCESS.2019.2910411.

Coh, Meredith. "Understanding Comas and Consciousness," The Baltimore Sun, Mar. 11, 2015, (11 pages), (article), [Retrieved from the Internet Apr. 8, 2022] <URL: https://www.baltimoresun.com/health/bs-hs-ask-the-expert-consciousness-20150311-story.html>.

Drees, Jackie. "30% of Johns-Hopkins in-Person Visits Will Convert to Telehealth Post Pandemic, CEO Says," Becker's Hospital Review, Jun. 22, 2020, (8 pages), (Article, Online), [Retrieved from the Internet Apr. 8, 2022] <URL: https://www.beckershospitalreview.com/telehealth/30-of-johns hopkins-in-person-visits-will-convert-to-telehealth-post-pandemic-ceo-says.html>.

Galle, Courtney E. "Walk-In Telehealth Visits Improve Access to Care, Wait Times, and Patient Satisfaction in Adult Patients with Non-Emergent Medical Conditions," Doctoral Dissertation, Mar. 2021 (63 pages), Brandman University.

Kucikiene, Domante et al. "The Impact of Music on the Bioelectrical Oscillations of the Brain," Acta Med Lituanica, vol. 25, No. 2, pp. 101-106, (Year: 2018), DOI:10.6001/actamedica.v25I2.3763, PMID: 30210244.

Masson, Francoise et al. "Epidemiology of Traumatic Comas: A Prospective Population-Based Study," Brain Injury, vol. 17, No. 4, Apr. 2003, pp. 279-293, (Published Online: Jul. 3, 2009), DOI: 10.1080/0269905021000030805. PMID: 12637181.

Serrano, Christina I. et al. "An Exploratory Study of Patient Acceptance of Walk-In Telemedicine Services For Minor Conditions," International Journal of Healthcare Information System and Informatics (IJHISI), vol. 4, No. 4, Oct.-Dec. 2009, pp. 1-35.

Vasilevskis, Eduard E. et al. "The Cost of ICU Delirium and Coma in the Intensive Care Unit Patient," Medical Care, vol. 56, No. 10, pp. 890-897, Oct. 2018, DOI: 10.1097/MLR.0000000000000975, PMID: 30179988.

Wong, C. et al. "Incidence, Aetiology, and Outcome of Non-Traumatic Coma: A Population Based Study," Archives of Disease in Childhood, vol. 84, No. 3, pp. 193-199, Mar. 2001, DOI: 10.1136/ads.84.3.193, PMID: 11207161.

Wong, Sze H. et al. "Telehealth and Screening Strategies in the Diagnosis and Management of Glaucoma," Journal of Clinical Medicine, vol. 10, No. 16:3452, Aug. 4, 2021, pp. 1-20, DOI: 10.3390.jcm10163452.

NonFinal Office Action for U.S. Appl. No. 17/643,030, dated Jun. 26, 2023, (31 pages), United States Patent and Trademark Office, US.

Kamran, et al., "A Survey of Recommender Systems and Their Application in Healthcare," Technical Journal, University of Engineering and Technology (UET), Taxila, Pakistan, vol. 20, No. IV, 2015, pp. 111-119 (Year: 2015).

Li, et al, "Learning and Optimization for Patient-Physician Matching in Specialty Care," Journal of Latex Class Files, vol. 6, No. 1, pp. 1-12, Jan. 2007.

Non-Final Rejection Mailed on Feb. 25, 2025 for U.S. Appl. No. 17/643,050, 49 page(s).

Wang, et al., "SPENT: A Successive POI Recommendation Method Using Similarity-Based POI Embedding and Recurrent Neural Network with Temporal Influence," 2019 IEEE International Conference on Big Data and Smart Computing (BigComp), Kyoto, Japan, 2019, pp. 1-8 (Year: 2019).

Final Rejection Mailed on Jun. 6, 2025 for U.S. Appl. No. 17/643,050, 64 page(s).

Parajay, et al., "A Neural Network Aided Real-time Hospital Recommendation System," Indonesian Journal of Science and Technology 5.2, pp. 217-235, (2020).

* cited by examiner

TRANSFER LEARNING TECHNIQUES FOR USING PREDICTIVE DIAGNOSIS MACHINE LEARNING MODELS TO GENERATE TELEHEALTH VISIT RECOMMENDATION SCORES

BACKGROUND

Various embodiments of the present invention address technical challenges related to performing predictive data analysis operations and address the efficiency and reliability shortcomings of various existing predictive data analysis solutions.

BRIEF SUMMARY

In general, embodiments of the present invention provide methods, apparatus, systems, computing devices, computing entities, and/or the like for performing predictive data analysis operations. For example, certain embodiments of the present invention utilize systems, methods, and computer program products that perform predictive data analysis operations by an end-to-end machine learning framework that performs at least the following steps/operations: (i) a service request data object is processed by a diagnosis prediction machine learning model to generate a probabilistic diagnosis data object, (ii) the probabilistic diagnosis data object is processed by the hybrid diagnosis-provider classification machine learning model to generate a variable-length classification for the service request data object, and (iii) the variable-length classification is processed by a telehealth visit recommendation scoring machine learning model to generate a telehealth visit recommendation score for the service request data object.

In accordance with one aspect, a method is provided. In one embodiment, the method comprises: identifying, using one or more processors, a probabilistic diagnosis data object associated with the service request data object, wherein the probabilistic diagnosis data object is generated by a diagnosis prediction machine learning model based at least in part on diagnosis input data associated with the service request data object; determining, using the one or more processors and a hybrid diagnosis-provider classification machine learning model and based at least in part on the probabilistic diagnosis data object and the provider data object, a variable-length classification for the service request data object, wherein: (i) the variable-length classification maps the service request data object to a variable-length subset of a plurality of candidate classes, and (ii) the plurality of candidate classes comprise one or more diagnosis-based classes, one or more provider-based classes, and one or more hybrid classes; determining, using the one or more processors and a telehealth visit recommendation scoring machine learning model and based at least in part on the variable-length classification, the telehealth visit recommendation score for the service request data object, wherein: (i) each candidate class is associated with a telehealth visit recommendation score, and (ii) the telehealth visit recommendation score is determined based at least in part on each telehealth visit recommendation score for the variable-length subset; performing, using the one or more processors, one or more prediction-based actions based at least in part on the telehealth visit recommendation score.

In accordance with another aspect, a computer program product is provided. The computer program product may comprise at least one computer-readable storage medium having computer-readable program code portions stored therein, the computer-readable program code portions comprising executable portions configured to: identify a probabilistic diagnosis data object associated with the service request data object, wherein the probabilistic diagnosis data object is generated by a diagnosis prediction machine learning model based at least in part on diagnosis input data associated with the service request data object; determine, using a hybrid diagnosis-provider classification machine learning model and based at least in part on the probabilistic diagnosis data object and the provider data object, a variable-length classification for the service request data object, wherein: (i) the variable-length classification maps the service request data object to a variable-length subset of a plurality of candidate classes, and (ii) the plurality of candidate classes comprise one or more diagnosis-based classes, one or more provider-based classes, and one or more hybrid classes; determine, using a telehealth visit recommendation scoring machine learning model and based at least in part on the variable-length classification, the telehealth visit recommendation score for the service request data object, wherein: (i) each candidate class is associated with a telehealth visit recommendation score, and (ii) the telehealth visit recommendation score is determined based at least in part on each telehealth visit recommendation score for the variable-length subset; perform one or more prediction-based actions based at least in part on the telehealth visit recommendation score.

In accordance with yet another aspect, an apparatus comprising at least one processor and at least one memory including computer program code is provided. In one embodiment, at least one memory and the computer program code may be configured to, with the processor, cause the apparatus to: identify a probabilistic diagnosis data object associated with the service request data object, wherein the probabilistic diagnosis data object is generated by a diagnosis prediction machine learning model based at least in part on diagnosis input data associated with the service request data object; determine, using a hybrid diagnosis-provider classification machine learning model and based at least in part on the probabilistic diagnosis data object and the provider data object, a variable-length classification for the service request data object, wherein: (i) the variable-length classification maps the service request data object to a variable-length subset of a plurality of candidate classes, and (ii) the plurality of candidate classes comprise one or more diagnosis-based classes, one or more provider-based classes, and one or more hybrid classes; determine, using a telehealth visit recommendation scoring machine learning model and based at least in part on the variable-length classification, the telehealth visit recommendation score for the service request data object, wherein: (i) each candidate class is associated with a telehealth visit recommendation score, and (ii) the telehealth visit recommendation score is determined based at least in part on each telehealth visit recommendation score for the variable-length subset; perform one or more prediction-based actions based at least in part on the telehealth visit recommendation score.

BRIEF DESCRIPTION OF THE DRAWINGS

Figure 1:
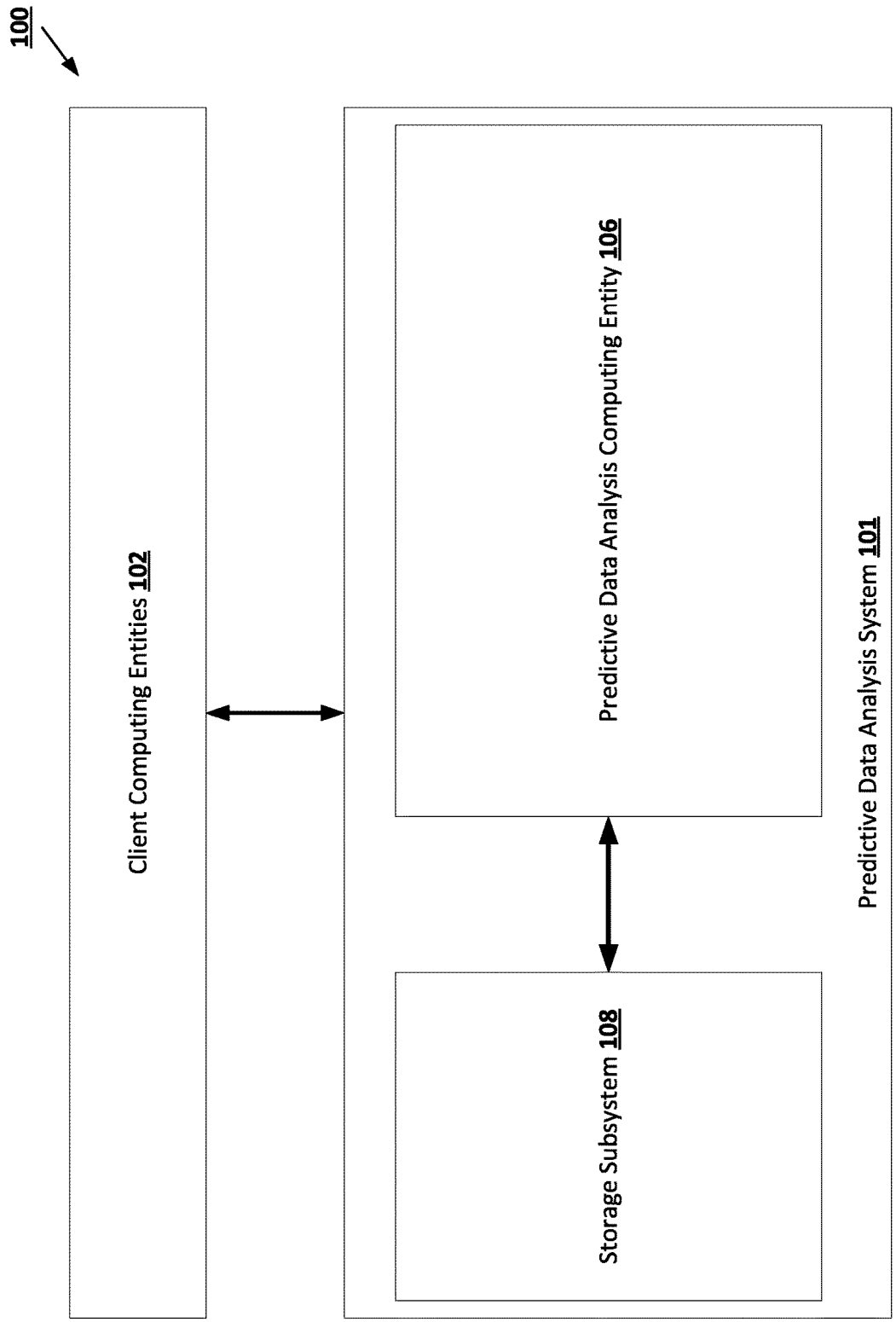

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
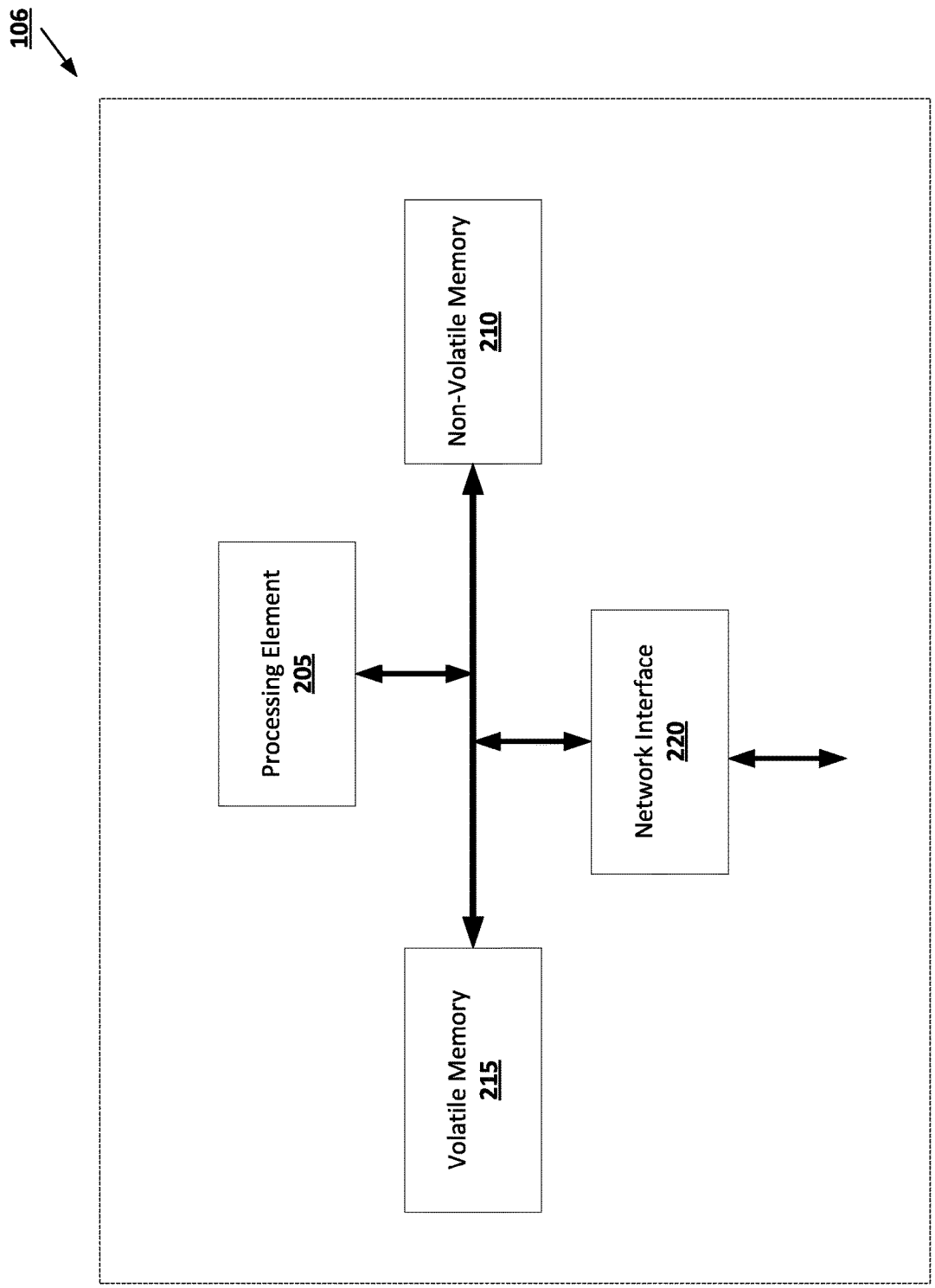

FIG. 2 provides an example predictive data analysis computing entity in accordance with some embodiments discussed herein.

Figure 3:
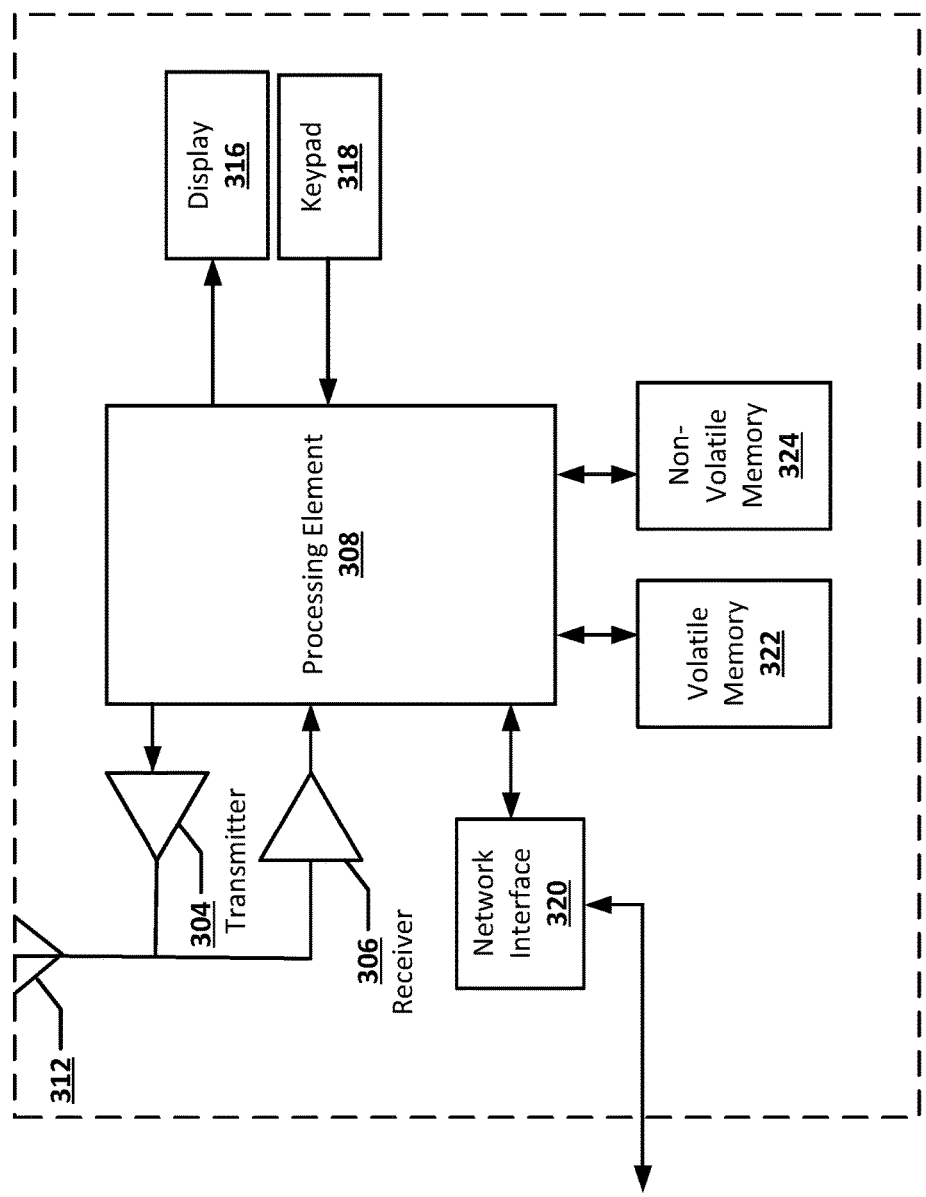

FIG. 3 provides an example client computing entity in accordance with some embodiments discussed herein.

Figure 4:
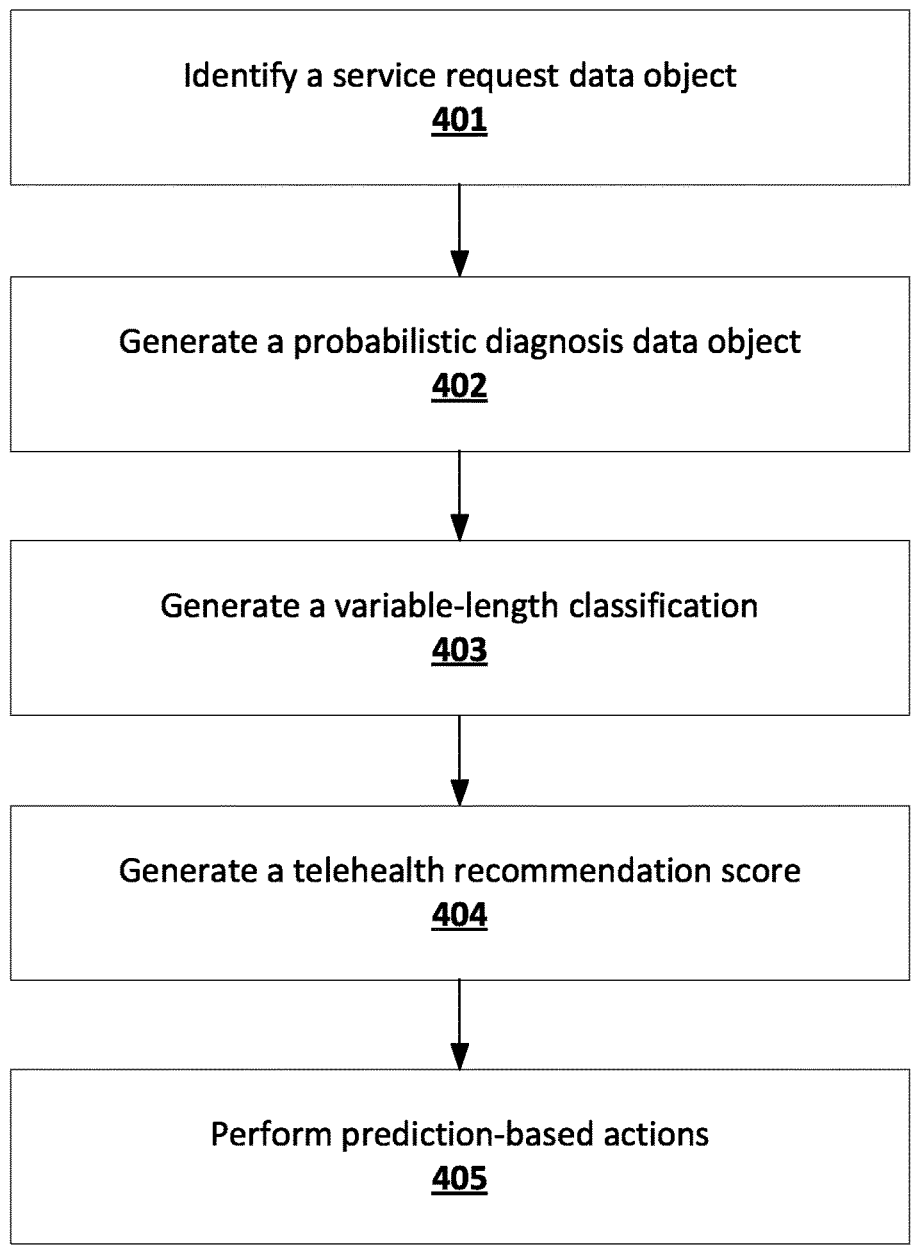

FIG. 4 is a flowchart diagram of an example process for determining a telehealth visit recommendation score in accordance with one or more optimal imbalance adjustment conditions in accordance with some embodiments discussed herein.

Figure 5:
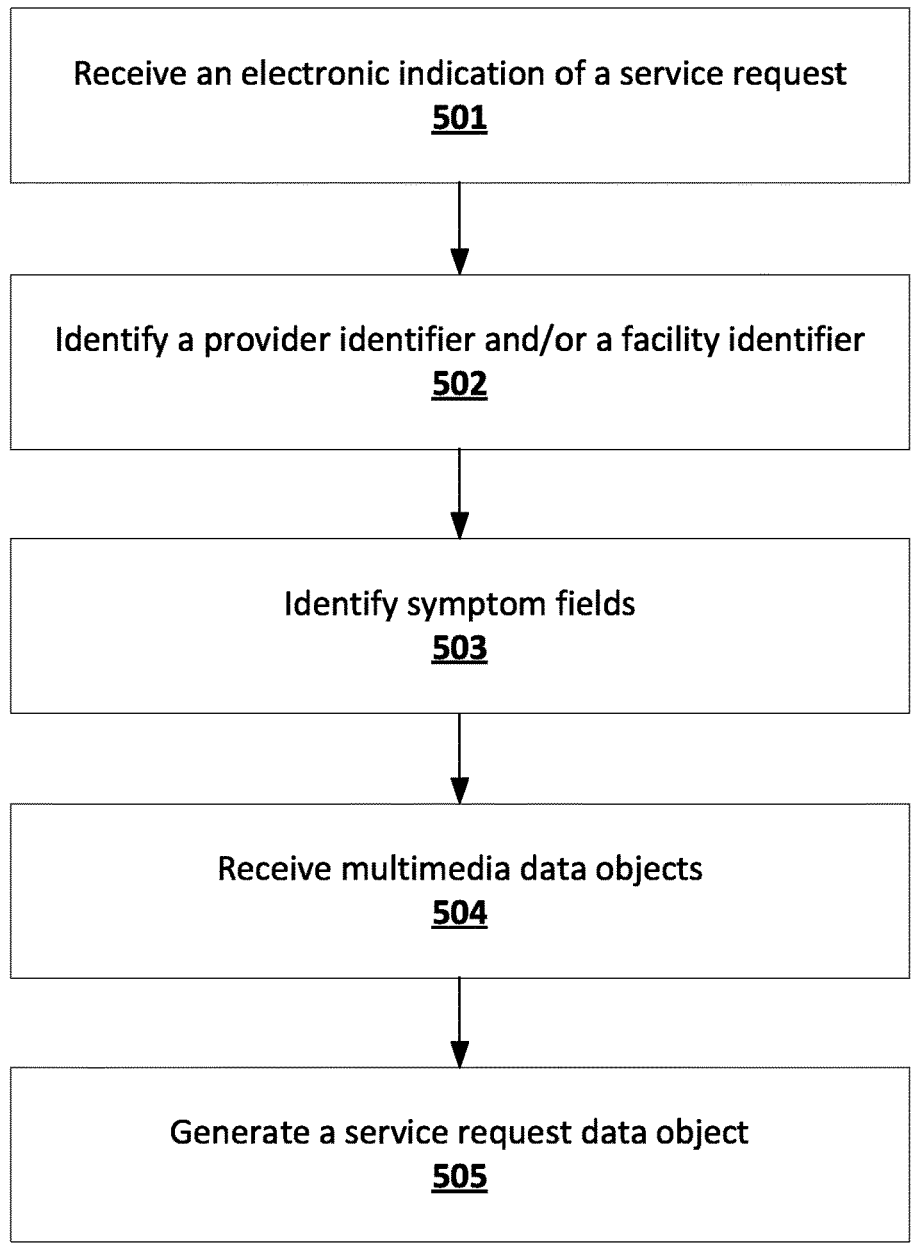

FIG. 5 is a flowchart diagram of an example process for generating a service request data object in accordance with some embodiments discussed herein.

Figure 6:
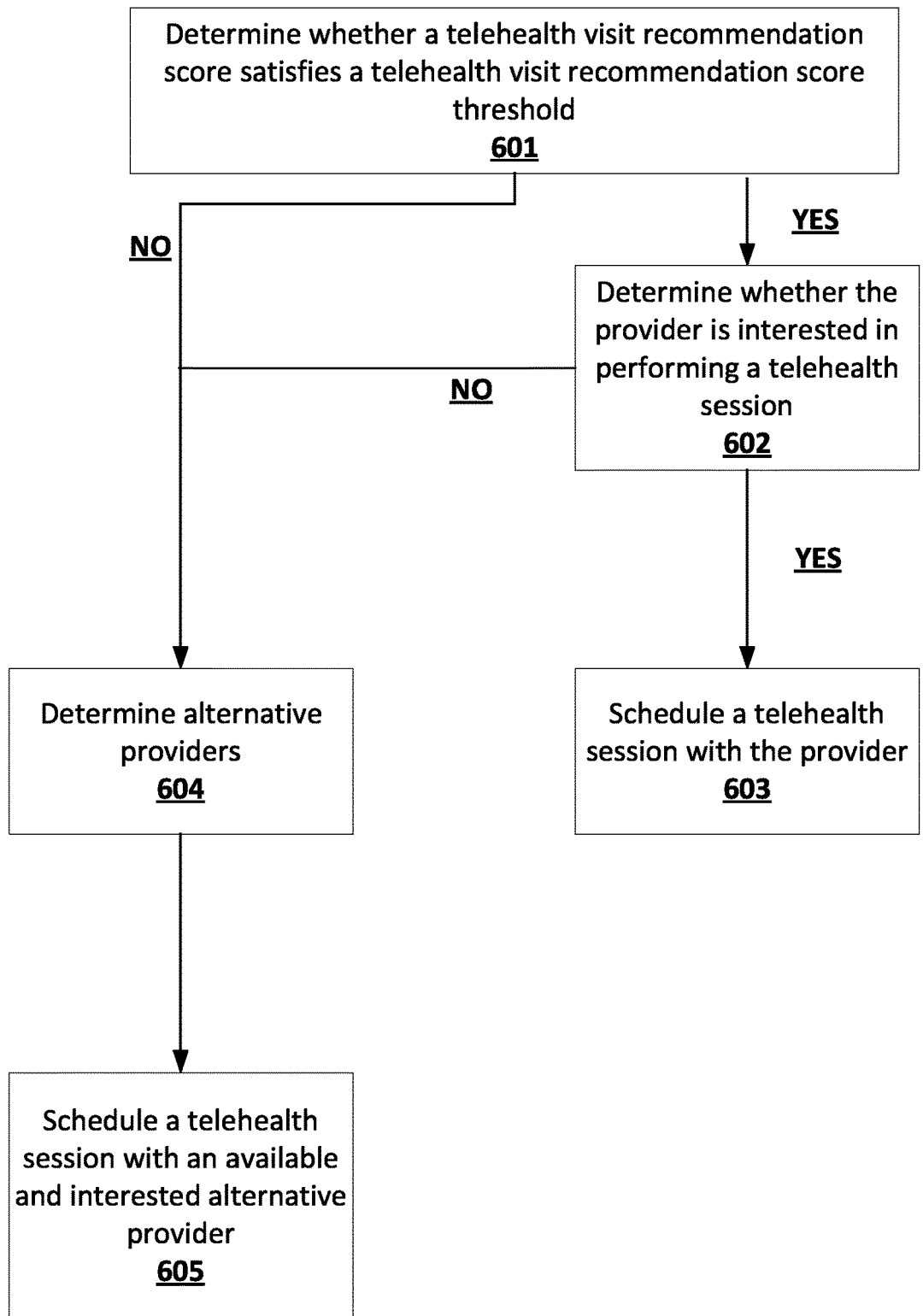

FIG. 6 is a flowchart diagram of an example process performing one or more prediction-based actions based at least in part on a telehealth recommendation score in accordance with some embodiments discussed herein.

Figure 7:

FIG. 7 provides an operational example of a user interface that includes facility navigational instructions in accordance with some embodiments discussed herein.

Figure 8:
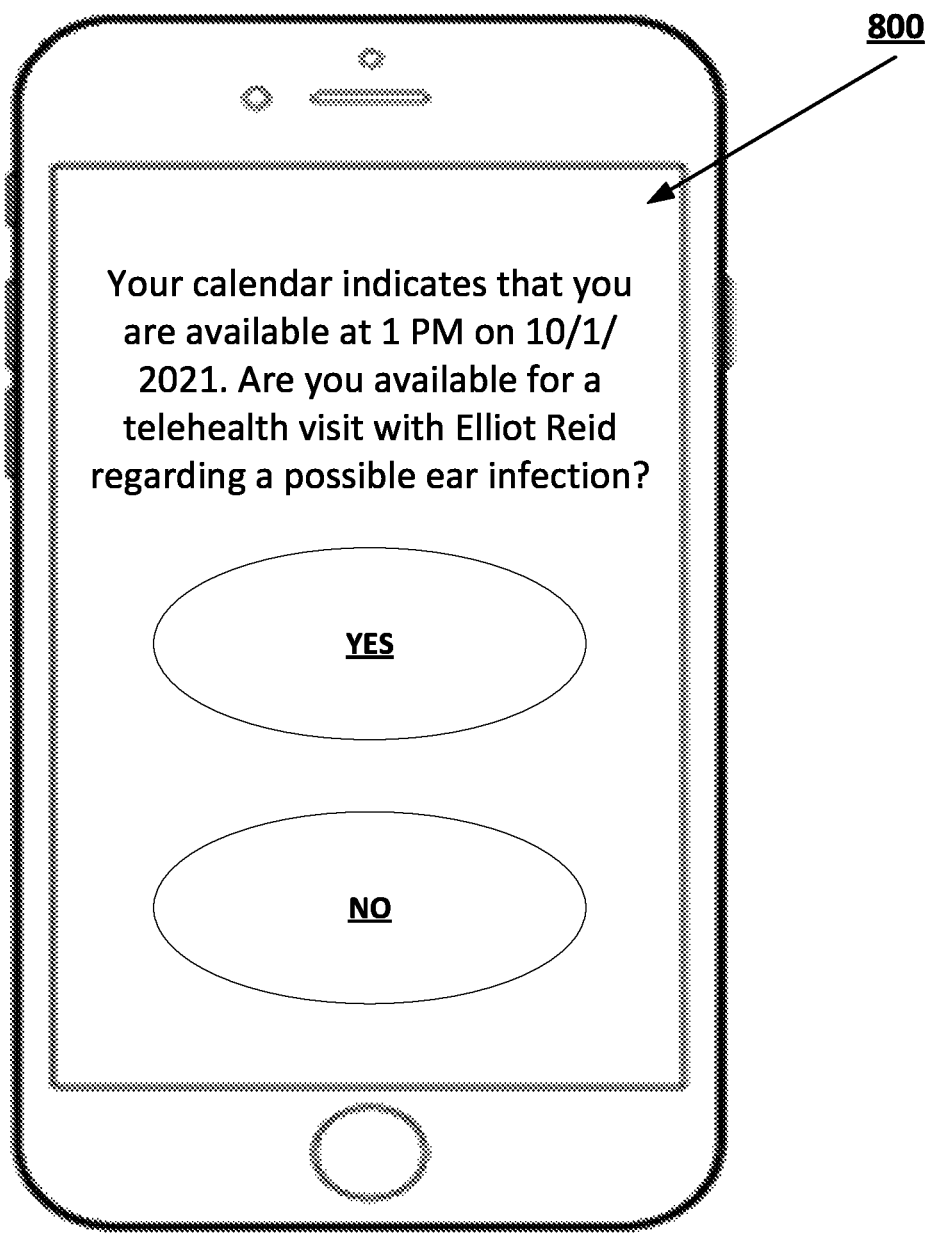

FIG. 8 provides an operational example of a user interface that includes a provider prompt in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis tasks.

I. OVERVIEW AND TECHNICAL IMPROVEMENTS

Various embodiments of the present invention introduce techniques for using the output of a diagnosis prediction machine learning model to generate a telehealth visit recommendation score. By using the noted techniques, various embodiments of the present invention enable using pretrained diagnosis prediction machine learning models to generate a telehealth visit recommendation score, thus reducing or avoiding the need for computationally expensive operations that are performed to generate diagnosis prediction machine learning models. In this way, various embodiments of the present invention reduce the number of computational operations performed to generate telehealth visit recommendation scores, thus improving the computational efficiency of predictive data analysis systems that are configured to generate telehealth visit recommendation scores and make important technical contributions to the field of predictive data analysis.

For example, various embodiments of the present invention utilize systems, methods, and computer program products that perform predictive data analysis operations by an end-to-end machine learning framework that performs at least the following steps/operations: (i) a service request data object is processed by a diagnosis prediction machine learning model to generate a probabilistic diagnosis data object, (ii) the probabilistic diagnosis data object is processed by the hybrid diagnosis-provider classification machine learning model to generate a variable-length classification for the service request data object, and (iii) the variable-length classification is processed by a telehealth visit recommendation scoring machine learning model to generate a telehealth visit recommendation score for the service request data object. By using the noted techniques, various embodiments of the present invention use a hybrid diagnosis-provider classification machine learning model and a telehealth visit recommendation scoring machine learning model to map the output of a diagnosis prediction machine learning model (e.g., a pretrained diagnosis prediction machine learning model) to a telehealth visit recommendation score, thus in some embodiments performing transfer learning to use a diagnosis prediction machine learning model to generate telehealth visit recommendation scores that are different from diagnosis scores generated by the diagnosis prediction machine learning model.

In some embodiments, the diagnosis prediction machine learning model is a pretrained machine learning model whose output with respect to a service request data object is used to generate a dynamic-length classification for the service request data object. In other words, various embodiments of the present invention perform transfer learning on a diagnosis prediction machine learning model by mapping the outputs of the diagnosis prediction machine learning model to a variable-length subset of a plurality of candidate classes. In some embodiments, a diagnosis prediction machine learning model (e.g., a pretrained diagnosis prediction machine learning model or an untrained diagnosis prediction machine learning model that is trained from scratch) is trained as part of an end-to-end machine learning framework that comprises the diagnosis prediction machine learning model, a hybrid diagnosis-provider classification machine learning model, and a telehealth visit recommendation scoring machine learning model.

An exemplary application of various embodiments of the present invention relates to determining when a telehealth visit for a patient may be beneficial as opposed to, for instance, conventional healthcare visits where a patient and provider directly interact. For example, if a patient has a contagious disease that a probabilistic diagnosis machine learning model is able to determine with a sufficient amount of certainty, it may be beneficial for the patient to use a telehealth facility. This allows for decreased exposure of healthcare providers, staff, other patients, and/or the like while still allowing the patient to interact with healthcare providers in a telehealth setting. In some embodiments, the following operations are performed: receiving data describing user need for medical care; receiving data describing a user location; receiving data describing user descriptions of symptoms; receiving data describing user-provided multimedia (e.g., videos, photographs, etc.); loading the above-described received data into a diagnostic agent; generating a probabilistic diagnosis using an existing/external probabilistic diagnostic model; providing a combination of the received data and the probabilistic diagnosis (e.g., probabilistic diagnosis plus patient location; probabilistic diagnosis plus patient health provider data, probabilistic diagnosis plus raw data provided by patient, etc.); using a telehealth visit engine to determine a telehealth visit prediction, prompting one or more telehealth facility staff for the potential telehealth visit, scheduling the telehealth visit, providing facility navigational instructions to a user device, and/or notifying a remote physician of the telehealth visit need.

II. DEFINITIONS

The term "diagnosis prediction machine learning model" may refer to a data construct that is configured to describe parameters, hyper-parameters, and/or defined operations of a model that is configured to process diagnosis input data for a service request data object in order to generate a probabilistic diagnosis data object for the service request data object. In some embodiments, the diagnosis prediction machine learning model is a pretrained machine learning model whose output with respect to a service request data object is used to generate a dynamic-length classification for the service request data object. In other words, various embodiments of the present invention perform transfer learning on a diagnosis prediction machine learning model by mapping the outputs of the diagnosis prediction machine learning model to a variable-length subset of a plurality of candidate classes. In some embodiments, a diagnosis prediction machine learning model (e.g., a pretrained diagnosis prediction machine learning model or an untrained diagnosis prediction machine learning model that is trained from scratch) is trained as part of an end-to-end machine learning framework that comprises the diagnosis prediction machine learning model, a hybrid diagnosis-provider classification machine learning model, and a telehealth visit recommendation scoring machine learning model, wherein the end-to-end machine learning framework may operate using at least the following steps/operations: (i) a service request data object is processed by the diagnosis prediction machine learning model to generate a probabilistic diagnosis data object, (ii) the probabilistic diagnosis data object is processed by the hybrid diagnosis-provider classification machine learning model to generate a variable-length classification for the service request data object, and (iii) the variable-length classification is processed by the telehealth visit recommendation scoring machine learning model to generate a telehealth visit recommendation score for the service request data object. In some embodiments, during training of the end-to-end machine learning framework, any trainable parameters of the diagnosis prediction machine learning model, the hybrid diagnosis-provider classification machine learning model, and the telehealth visit recommendation scoring machine learning model are trained based at least in part on inferred telehealth visit recommendation scores for service request data objects and ground-truth telehealth recommendation outcomes for the service request data objects as determined based at least in part on historical data associated with the service request data object. For example, if an inferred telehealth visit recommendation score for a service request data object is 0.4 but the ground-truth telehealth recommendation outcome for the service request data object describes an affirmative telehealth visit outcome (e.g., describes that the patient was recommended a telehealth visit in response to the service request data object), then a deviation measure of 1−0.4=0.6 may be used as part of an error measure that is used to train the end-to-end machine learning framework by updating any trainable parameters of the diagnosis prediction machine learning model, the hybrid diagnosis-provider classification machine learning model, and the telehealth visit recommendation scoring machine learning model in a manner that is configured to optimize the error measure. In some embodiments, inputs to a diagnosis prediction machine learning model include one or more vectors describing diagnostic input data for a service request data object, while outputs of a diagnosis prediction machine learning model include a vector describing n diagnostic probabilities for m candidate conditions, where those candidate conditions having a threshold-satisfying diagnostic probability may be deemed to be a diagnosed condition described by the vector.

The term "probabilistic diagnosis data object" may refer to a data construct that is configured to describe, for a particular service request data object that is associated with particular diagnosis input data, a set of diagnosed conditions along with a diagnosis probability for each diagnosed condition. For example, a probabilistic diagnosis data object may describe that a service request data object is associated with a diagnosis $D_1$ with the probability $P_1$, a diagnosis $D_2$ with the probability $P_2$, and so on. In some embodiments, the probabilistic diagnosis data object is generated by: (i) obtaining a set of raw diagnosis probabilities for a set of conditions from a diagnosis prediction machine learning model, (ii) normalizing the set of raw diagnosis probabilities to generate the set of diagnosis probabilities for the set of conditions, and (iii) generating the probabilistic diagnosis data object based at least in part on the set of diagnosis probabilities. For example, in some embodiments, the diagnosis prediction machine learning model may include n machine learning components, where each machine learning component is configured to generate a diagnosis probability for a condition of n conditions. In the noted example, the output of each machine learning component may have a different range. Thus, to generate the diagnosis probabilities described by the probabilistic diagnosis data object, the n diagnosis probabilities generated by the n machine learning components may be normalized to have a unified range (e.g., a unified range of [0, 1]), and then the normalized diagnosis probabilities may be used to generate the diagnosis probability data object. For example, the diagnosis probability data object may describe all n normalized diagnosis probabilities, the top m of the normalized diagnosis probabilities (where m may be a predefined value that is smaller than n), and/or those normalized diagnosis probabilities that satisfy (e.g., exceed) a normalized diagnosis probability threshold. In some embodiments, the diagnosis probabilities described by a probabilistic diagnosis data object are determined based at least in part on diagnosis input data associated with a corresponding service request data object, e.g., one or more service fields associated with the service request data object, one or more medical history fields associated with a patient identifier that is associated with the service request data object, and/or the like.

The term "hybrid diagnosis-provider classification machine learning model" may refer to a data construct that is configured to describe parameters, hyper-parameters, and/or defined operations of a model that is configured to process a probabilistic diagnosis data object for a service request data object and a provider data object for a service request data object to generate a variable-length classification for the service request data object. In some embodiments, the hybrid diagnosis-provider classification machine learning model may be configured to: (i) map the probabilistic diagnosis data object for a service request data object to a variable-length subset of one or more diagnosis-based classes, (ii) map the provider data object for a service request data object to a variable-length subset of one or more provider-based classes, and/or (iii) map a combination of the probabilistic diagnosis data object for a service request data object and a provider data object for a service request data object to a variable-length subset of one or more hybrid classes. In some of the noted embodiments, given a service request data object $S_1$ that is associated with a probabilistic data object $PD_1$ and a provider data object $P_1$, the hybrid diagnosis-provider classification machine learning model may determine: (i) of a set of available classes for the $P_1$, e of the available classes that $P_1$ actually corresponds to (where e is a variable number), (ii) of a set of available classes for the $PD_1$, f of the available classes that $PD_1$ actually corresponds to (where f is a variable number), and (iii) of a set of available classes for the combination $P_1$-$PD_1$, g of the available classes that $P_1$-$PD_1$ actually corresponds to (where g is a variable number). In other words, the hybrid diagnosis-provider classification machine learning model may be configured to determine, based at least in part on $P_1$ and $PD_1$, a variable-length classification for $S_1$, where the variable-length classification maps $S_1$ to a variable-length subset of a plurality of candidate classes, where the plurality of candidate classes comprise one or more diagnosis-based classes, one or more provider-based classes, and one or more hybrid classes. In some embodiments, inputs to a hybrid diagnosis-provider classification machine learning model include a vector describing a probabilistic diagnosis data object and one or more vectors describing data extracted from a provider data object, while outputs of a hybrid diagnosis-provider classification machine learning model include a vector that describes, for each candidate classification, whether the variable-length classification generated by the hybrid diagnosis-provider classification machine learning model indicates a mapping of the candidate classification to a particular service request data object.

The term "variable-length classification" may refer to a data construct that is configured to describe whether an input data object (e.g., a service request data object) maps to any of a set of candidate classes. In some embodiments, the variable-length classification maps a service request data object to h candidate classes of a set of candidate classes, where h>=0. In some embodiments, the set of candidate classes comprise one or more diagnosis-based classes, one or more provider-based classes, and one or more hybrid classes, which are described in greater detail below.

The term "diagnosis-based class" may refer to a data construct that is configured to describe an available label for a service request data object, where the service request data object may be mapped to the available label if a probabilistic diagnosis data object for the service request data object satisfies one or more conditions associated with the available label. Examples of diagnosis-based classes include a contagion class to which a service request data object is mapped if the probabilistic diagnosis data object for the service request data object describes a threshold-satisfying diagnosis probability for a diagnosed condition that is listed as being non-contagious, mildly contagious, moderately contagious, and/or severely contagious. Diagnosis-based classes may also include a user risk class to which a service request data object is mapped if the probabilistic diagnosis data object for the service request data object describes a threshold-satisfying diagnosis probability for a diagnosed condition that is listed as being non-risky, mildly risky, moderately risky, and/or severely risky. Diagnosis-based classes may also include a specialty class to which a service request data object is mapped if the probabilistic diagnosis data object for the service request data object describes a threshold-satisfying diagnosis probability for a diagnosed condition that is listed as being recommended to be examined by a specialist provider to effectively diagnosis and/or treat. In some embodiments, the specialty class may be divided into one or more specialty classes, such as a general specialty class, endocrinologist specialty class, neurologist specialty class, dermatologist specialty class, and/or the like. Diagnosis-based classes may also include a diagnosis confidence class to which a service request data object is mapped if the probabilistic diagnosis data object for the service request data object describes a threshold-satisfying diagnosis probability for a diagnosed condition that is based at least in part on an associated diagnosis probability, such as a high diagnosis confidence class, moderate diagnosis confidence class, and low diagnosis confidence class. In some embodiments, when a probabilistic diagnosis data object for a service request data object includes n diagnosed probabilities for n conditions, then mapping the service request data object to a diagnosis-based class comprises: (i) determining a related subset of the n diagnosed conditions that are listed as being related to the diagnosis-based class (e.g., for a contagion class, determining a related subset of the n diagnosed conditions that are listed as being non-contagious, mildly contagious, moderately contagious, and/or severely contagious), (ii) combining (e.g., summing, averaging, and/or the like) each diagnosis probability for a diagnosis condition in the related subset for the diagnosis-based class to determine a classification score for the diagnosis-based class, and (iii) mapping the service request data object to the diagnosis-based class if the classification score for the diagnosis-based class satisfies (e.g., exceeds) a classification score threshold.

The term "provider-based class" may refer to a data construct that is configured to describe an available label for a service request data object, where the service request data object may be mapped to the available label if a provider data object for the service request data object satisfies one or more conditions associated with the available label. Examples of provider-based classes include an availability class to which a service request data object is mapped if a provider schedule described by the provider data object for the service request data object includes available time slots for scheduling a service appointment associated with the service request data object.

The term "hybrid diagnosis class" may refer to a data construct that is configured to describe an available label for a service request data object, where the service request data object may be mapped to the available label if a combination of the provider data object associated with the service request data object and the probabilistic diagnosis data object associated with the service request data object satisfies one or more conditions associated with the available label. Examples of hybrid diagnosis classes include a facility equipment class that is mapped to a service request data object if a facility is equipped with the tools and/or equipment necessary to diagnose and/or test a patient in relation to one or more diagnosed conditions described by the probabilistic diagnosis data object for the service request data object.

The term "telehealth visit recommendation scoring machine learning model" may refer to a data construct that is configured to describe parameters, hyper-parameters, and/or defined operations of a model that is configured to process a variable-length classification for a service request data object to generate a telehealth visit recommendation score for the service request data object. In some embodiments, the telehealth visit recommendation scoring machine learning model combines each telehealth visit recommendation score for a variable-length subset of candidate classifications that are associated with the variable-length classification to generate the telehealth visit recommendation score for the service request data object. For example, consider a service request data object that is associated with a variable-length classification that describes that the service request data object is associated with candidate classifications $C_1$-$C_3$, where the candidate classifications $C_1$-$C_3$ are associated with telehealth visit recommendation scores $R_1$-$R_3$ respectively. In some embodiments, the telehealth visit recommendation score for the service request data object may be determined based at least in part on a combination of $C_1$-$C_3$ (e.g., based at least in part on $C_1+C_2+C_3/3$). In some embodiments, the telehealth visit recommendation score for a candidate classification may describe a degree of correlation between a mapping of the candidate classification to a service request data object and whether a telehealth visit should be scheduled with respect to the service request data object. In some embodiments, each telehealth visit recommendation score for a candidate classification is a trained parameter of the telehealth visit recommendation scoring machine learning model. In some embodiments, inputs to a telehealth visit recommendation scoring machine learning model comprise a vector describing a variable-length classification, while outputs of a telehealth visit recommendation scoring machine learning model comprise a vector and/or an atomic value describing a telehealth visit recommendation score.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a scripting language, a database query or search language, and/or a report writing language. In one or more example embodiments, a software component comprising instructions in one of the foregoing examples of programming languages may be executed directly by an operating system or other software components without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid-state card (SSC), solid-state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read-only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises a combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing predictive data analysis. The architecture 100 includes a predictive data analysis system 101 configured to receive predictive data analysis requests from client computing entities 102, process the predictive data analysis requests to generate predictions, provide the generated predictions to the client computing entities 102, and automatically perform prediction-based actions based at least in part on the generated predictions. An example of a prediction-based action that can be performed using the predictive data analysis system 101 is processing a request for medical services by scheduling a telehealth visit with a physician and/or medical practitioner.

In some embodiments, predictive data analysis system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically perform prediction-based actions based at least in part on the generated predictions.

The storage subsystem 108 may be configured to store input data used by the predictive data analysis computing entity 106 to perform predictive data analysis as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application-specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the predictive data analysis computing entity 106 and/or various other computing entities.

In another embodiment, the client computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

As described below, various embodiments of the present invention introduce techniques for using the output of a diagnosis prediction machine learning model to generate a telehealth visit recommendation score. By using the noted techniques, various embodiments of the present invention enable using pretrained diagnosis prediction machine learning models to generate a telehealth visit recommendation score, thus reducing or avoiding the need for computationally expensive operations that are performed to generate diagnosis prediction machine learning models. In this way, various embodiments of the present invention reduce the number of computational operations performed to generate telehealth visit recommendation scores, thus improving the computational efficiency of predictive data analysis systems that are configured to generate telehealth visit recommendation scores and make important technical contributions to the field of predictive data analysis.

FIG. 4 is a flowchart diagram of an example process 400 for determining a telehealth visit recommendation score for a service request data object. Via the various steps/operations of the process 400, a predictive data analysis computing entity 106 can use a hybrid diagnosis-provider classification machine learning model and a telehealth visit recommendation scoring machine learning model to map the output of a diagnosis prediction machine learning model (e.g., a pretrained diagnosis prediction machine learning model) to a telehealth visit recommendation score, thus in some embodiments performing transfer learning to use a diagnosis prediction machine learning model to generate telehealth visit recommendation scores that are different from diagnosis scores generated by the diagnosis prediction machine learning model.

The process 400 begins at step/operation 401 when the predictive data analysis computing entity 106 identifies the service request data object. In some embodiments, the service request data object describes diagnosis input data (e.g., symptom data, medical history data, and/or the like) associated with a service request (e.g., a request for medical services), a patient/service recipient identifier for the service request, a provider (e.g., medical provider) identifier for the service request, a medical facility identifier for the service request, one or more multimedia objects associated with the service request.

In some embodiments, step/operation 401 may be performed in accordance with the process that is depicted in FIG. 5. The process that is depicted in FIG. 5 begins at step/operation 501 when the predictive data analysis computing entity 106 receives an electronic indication that a service (e.g., a healthcare service) is requested. The electronic indication may be generated in response to a medical appointment creation request that is generated using a smartphone or desktop application, in response to a telephone call, and/or the like.

At step/operation 502, the predictive data analysis computing entity 106 identifies a provider identifier and/or a facility identifier for the service request. In some embodiments, the provider identifier and/or the facility identifier may be explicitly provided as part of the service request. In some embodiments, the provider identifier and/or the facility identifier may be inferred based at least in part on patient preference data maintained by the predictive data analysis computing entity 106.

At step/operation 503, the predictive data analysis computing entity 106 identifies one or more symptom fields associated with a patient identifier for the service request. A patient may use external third-party application provider applications or payer applications to enter symptoms (e.g., by using drop-down selection, free-form text, question-and-answer decision trees, and/or in other manners). In some embodiments, if the service request includes free-form text, the service request is processed in accordance with a natural language processing machine learning model in order to detect one or more diagnosis codes, one or more symptom codes, and/or one or more procedure codes in the free form text. In some embodiments, the one or more symptom fields are identified by a process that includes at least the following steps/operations: (i) for each symptom of a plurality of candidate symptoms, generating a symptom presence score that is generated by the natural language processing machine learning model via processing the free-form text using the natural language processing machine learning model and a symptom historical score that is generated by a relative occurrence frequency of the symptom within electronic health record (EHR) data of the patient identifier, (ii) for each symptom, generating a combined symptom score based at least in part on the symptom presence score for the symptom and historical symptom score for the symptom, and (iii) determining the one or more symptom fields for the patient identifier based at least in part on each symptom having a threshold-satisfying combined symptom score.

At step/operation 504, the predictive data analysis computing entity 106 optionally receives one or more multimedia data objects (e.g., videos, photographs, Digital Imaging and Communications in Medicine (DICOM) files and/or the like) for the service request. Examples of multi-media data objects include a magnetic resonance imaging (MRI) report, a computed tomography (CT) scan, a colonoscopy image, one or more DICOM files, or other professionally-derived images. The multimedia data objects may be uploaded by an end-user that is generating the service request.

At step/operation 505, the predictive data analysis computing entity 106 determines the service request data object. In some embodiments, the predictive data analysis computing entity 106 combines at least one of the provider identifiers, the facility identifier, the symptom fields, and the multimedia data objects in order to generate the service request data object. In some embodiments, the service request data object describes diagnostic input data associated with the service request data object, such as one or more symptom fields associated with the service request data object, one or more medical history fields associated with the service request data object, and/or the like.

Returning to FIG. 4, at step/operation 402, the predictive data analysis computing entity 106 generates a probabilistic diagnosis data object for the service request data object. In some embodiments, the predictive data analysis computing entity 106 loads diagnosis input data associated with the service request data object into a diagnostic agent (e.g., a cloud-based diagnosis agent), and obtains the probabilistic diagnosis data object from the diagnostic agent in response to the loading of the diagnosis input data.

In some embodiments, a probabilistic diagnosis data object describes, for a particular service request data object that is associated with a particular diagnosis input data, a set of diagnosed conditions along with a diagnosis probability for each diagnosed condition. For example, a probabilistic diagnosis data object may describe that a service request data object is associated with a diagnosis $D_1$ with the probability $P_1$, a diagnosis $D_2$ with the probability $P_2$, and so on. In some embodiments, the probabilistic diagnosis data object is generated by: (i) obtaining a set of raw diagnosis probabilities for a set of conditions from a diagnosis prediction machine learning model, (ii) normalizing the set of raw diagnosis probabilities to generate the set of diagnosis probabilities for the set of conditions, and (iii) generating the probabilistic diagnosis data object based at least in part on the set of diagnosis probabilities.

In some embodiments, the probabilistic diagnosis data object for a service request data object is generated by a diagnosis prediction machine learning model based at least in part on diagnosis input data associated with the service request data object. The diagnosis prediction machine learning model may be configured to process diagnosis input data for a service request data object in order to generate a probabilistic diagnosis data object for the service request data object. In some embodiments, the diagnosis prediction machine learning model is a pretrained machine learning model whose output with respect to a service request data object is used to generate a dynamic-length classification for the service request data object. In other words, various embodiments of the present invention perform transfer learning on a diagnosis prediction machine learning model by mapping the outputs of the diagnosis prediction machine learning model to a variable-length subset of a plurality of candidate classes.

In some embodiments, the diagnosis prediction machine learning model may include n machine learning components, where each machine learning component is configured to generate a diagnosis probability for each condition of n conditions. In the noted example, the output of each machine learning component may have a different range. Thus, to generate the diagnosis probabilities described by the probabilistic diagnosis data object, the n diagnosis probabilities generated by the n machine learning components may be normalized to have a unified range (e.g., a unified range of [0, 1]), and then the normalized diagnosis probabilities may be used to generate the diagnosis probability data object. For example, the diagnosis probability data object may describe all n normalized diagnosis probabilities, the top m of the normalized diagnosis probabilities (where m may be a predefined value that is smaller than n), and/or those normalized diagnosis probabilities that satisfy (e.g., exceed) a normalized diagnosis probability threshold. In some embodiments, the diagnosis probabilities described by a probabilistic diagnosis data object are determined based at least in part on diagnosis input data associated with a corresponding service request data object, e.g., one or more service fields associated with the service request data object, one or more medical history fields associated with a patient identifier that is associated with the service request data object, and/or the like.

In some embodiments, a diagnosis prediction machine learning model (e.g., a pretrained diagnosis prediction machine learning model or an untrained diagnosis prediction machine learning model that is trained from scratch) is trained as part of an end-to-end machine learning framework that comprises the diagnosis prediction machine learning model, a hybrid diagnosis-provider classification machine learning model, and a telehealth visit recommendation scoring machine learning model, wherein the end-to-end machine learning framework may operate using at least the following steps/operations: (i) a service request data object is processed by the diagnosis prediction machine learning model to generate a probabilistic diagnosis data object, (ii) the probabilistic diagnosis data object is processed by the hybrid diagnosis-provider classification machine learning model to generate a variable-length classification for the service request data object, and (iii) the variable-length classification is processed by the telehealth visit recommendation scoring machine learning model to generate a telehealth visit recommendation score for the service request data object.

In some embodiments, during training of the end-to-end machine learning framework, any trainable parameters of the diagnosis prediction machine learning model, the hybrid diagnosis-provider classification machine learning model, and the telehealth visit recommendation scoring machine learning model are trained based at least in part on inferred telehealth visit recommendation scores for service request data objects and ground-truth telehealth visit outcomes for the service request data objects as determined based at least in part on historical data associated with the service request data object. For example, if an inferred telehealth visit recommendation score for a service request data object is 0.4 but the ground-truth telehealth visit outcome for the service request data object describes an affirmative telehealth visit outcome (e.g., describes that the patient was scheduled for a telehealth visit in response to the service request data object), then a deviation measure of $1-0.4=0.6$ may be used as part of an error measure that is used to train the end-to-end machine learning framework by updating any trainable parameters of the diagnosis prediction machine learning model, the hybrid diagnosis-provider classification machine learning model, and the telehealth visit recommendation scoring machine learning model in a manner that is configured to optimize the error measure.

At step/operation 403, the predictive data analysis computing entity 106 determines a variable-length classification for the service request data object based at least in part on the probabilistic diagnosis data object for the service request data object and the provider data object for the service request data object. In some embodiments, step/operation 403 may be performed by a telehealth visit agent (e.g., a cloud-based telehealth visit agent).

In some embodiments, the hybrid diagnosis-provider classification machine learning model may be configured to: (i) map the probabilistic diagnosis data object for a service request data object to a variable-length subset of one or more diagnosis-based classes, (ii) map the provider data object for a service request data object to a variable-length subset of one or more provider-based classes, and/or (iii) map a combination of the probabilistic diagnosis data object for a service request data object and a provider data object for a service request data object to a variable-length subset of one or more hybrid classes. In some of the noted embodiments, given a service request data object $S_1$ that is associated with a probabilistic data object $PD_1$ and a provider data object $P_1$, the hybrid diagnosis-provider classification machine learning model may determine: (i) of a set of available classes for the $P_1$, e of the available classes that $P_1$ actually corresponds to (where e is a variable number), (ii) of a set of available classes for the $P_1$, f of the available classes that $PD_1$ actually corresponds to (where f is a variable number), and (iii) of a set of available classes for the combination $P_1$-$PD_1$, g of the available classes that $P_1$-$PD_1$ actually corresponds to (where g is a variable number). In some embodiments, the hybrid diagnosis-provider classification machine learning model is trained using training data determined based at least in part on historical telehealth visit arrangements (e.g., such that, if a proposed telehealth visit has occurred in the past, the training entry describing features of the proposed telehealth visit is assigned a training label of one and otherwise the training entry is assigned a training label of zero).

In some embodiments, the probabilistic diagnosis data object comprises a sequence of diagnosis probabilities for a sequence of conditions, and the hybrid diagnosis-provider classification machine learning model comprises a recurrent neural network machine learning model (e.g., a long-short term memory neural network machine learning model, a gated recurrent unit machine learning model, and/or the like) that is configured to, at each timestep of a sequence of timesteps, process a corresponding diagnosis probability in the sequence of diagnosis probabilities in accordance with trained parameters of the recurrent neural network machine learning model to generate a hidden state for the timestep. In some embodiments, during each non-initial timestamp, generating the hidden state of the non-initial timestamp comprises processing a corresponding diagnosis probability in the sequence of diagnosis probabilities and a hidden state of an immediately preceding hidden state in accordance with trained parameters of the recurrent neural network machine learning model to generate a hidden state for the non-initial timestep. In some embodiments, during an initial timestamp, generating the hidden state of the initial timestamp comprises processing a corresponding diagnosis probability in the sequence of diagnosis probabilities and a null hidden state of an immediately preceding hidden state in accordance with trained parameters of the recurrent neural network machine learning model to generate a hidden state for the initial timestep. In some embodiments, the variable-length subset of a plurality of candidate classes is determined based at least in part on a hidden state of a final timestamp of the sequence of timestamps. In some embodiments, given a provider identifier that is associated with a provider specialty condition, the sequence of conditions is determined such that the provider specialty condition is the first condition in the sequence and each n+1th condition in the sequence is deemed more similar to the provider specialty condition than a preceding nth condition. Accordingly, in some embodiments, a set of n conditions may be ordered based at least in part on similarity to the provider specialty condition to generate the sequence of conditions.

In some embodiments, the hybrid diagnosis-provider classification machine learning model comprises n recurrent neural network machine learning models each associated with a diagnosis-based class. In some embodiments, the probabilistic diagnosis data object is used to determine, for each diagnosis-based class, a sequence of diagnosis probabilities for a sequence of conditions arranged in a sequence ordering associated with the diagnosis-based class. In some embodiments, for each diagnosis-based class, the sequence of diagnosis probabilities arranged in a sequence ordering associated with the diagnosis-based class is processed by via the recurrent neural network machine learning model via a sequence of timestamps that is associated with the candidate class to generate a class probability for the candidate class, where the class probability is determined based an output of a final timestep. In some embodiments, the top m candidate classes having the highest classes probabilities are selected as the variable-length subset of the diagnosis-based classes.

For example, given a particular recurrent neural network machine learning model (e.g., a long-short term memory neural network machine learning model, a gated recurrent unit machine learning model, and/or the like) that is associated with a particular diagnosis-based class, the diagnosis probabilities of the probabilistic diagnosis data object as arranged based at least in part on a sequence ordering associated with the diagnosis-based class may be processed by the recurrent neural network machine learning model to generate the class probabilities for the diagnosis-based class. In some embodiments, during each non-initial timestamp, generating the hidden state of the non-initial timestamp comprises processing a corresponding diagnosis probability in the sequence of diagnosis probabilities and a hidden state of an immediately preceding hidden state in accordance with trained parameters of the recurrent neural network machine learning model to generate a hidden state for the non-initial timestamp. In some embodiments, during an initial timestamp, generating the hidden state of the initial timestamp comprises processing a corresponding diagnosis probability in the sequence of diagnosis probabilities and a null hidden state of an immediately preceding hidden state in accordance with trained parameters of the recurrent neural network machine learning model to generate a hidden state for the initial timestamp. In some embodiments, the class probability for the diagnosis-based class is determined based at least in part on a hidden state of a final timestamp of the sequence of timestamps for a recurrent neural network machine learning model that is associated with the noted diagnosis-based class.

In some embodiments, a service request data object is mapped to a variable-length classification by using a hybrid diagnosis-provider classification machine learning model that is configured to process a probabilistic diagnosis data object for a service request data object and a provider data object for a service request data object to generate a variable-length classification for the service request data object. In some embodiments, the hybrid diagnosis-provider classification machine learning model may be configured to: (i) map the probabilistic diagnosis data object for a service request data object to a variable-length subset of one or more diagnosis-based classes, (ii) map the provider data object for a service request data object to a variable-length subset of one or more provider-based classes, and/or (iii) map a combination of the probabilistic diagnosis data object for a service request data object and a provider data object for a service request data object to a variable-length subset of one or more hybrid classes. In some embodiments, the hybrid diagnosis-provider classification machine learning model may be configured to determine, based at least in part on a provider identifier $P_1$ and a probabilistic diagnosis $PD_1$ for a service request data object $S_1$, a variable-length classification for $S_1$, where the variable-length classification maps $S_1$ to a variable-length subset of a plurality of candidate classes, where the plurality of candidate classes comprise one or more diagnosis-based classes, one or more provider-based classes, and one or more hybrid classes.

In some embodiments, a variable-length classification maps a service request data object to h candidate classes of a set of candidate classes, where h>=0. In some embodiments, the set of candidate classes comprise one or more diagnosis-based classes, one or more provider-based classes, and one or more hybrid classes, as further described below.

A diagnosis-based class may be an available label for a service request data object, where the service request data object may be mapped to the available label if a probabilistic diagnosis data object for the service request data object satisfies one or more conditions associated with the available label. Examples of diagnosis-based classes include a contagion class to which a service request data object is mapped if the probabilistic diagnosis data object for the service request data object describes a threshold-satisfying diagnosis probability for a diagnosed condition that is listed as being non-contagious, mildly contagious, moderately contagious, and/or severely contagious. Diagnosis-based classes may also include a user risk class to which a service request data object is mapped if the probabilistic diagnosis data object for the service request data object describes a threshold-satisfying diagnosis probability for a diagnosed condition that is listed as being non-risky, mildly risky, moderately risky, and/or severely risky. Diagnosis-based classes may also include a specialty class to which a service request data object is mapped if the probabilistic diagnosis data object for the service request data object describes a threshold-satisfying diagnosis probability for a diagnosed condition that is listed as being recommended to be examined by a specialist provider to effectively diagnosis and/or treat. In some embodiments, the specialty class may be divided into one or more specialty classes, such as a general specialty class, endocrinologist specialty class, neurologist specialty class, dermatologist specialty class, and/or the like. Diagnosis-based classes may also include a diagnosis confidence class to which a service request data object is mapped if the probabilistic diagnosis data object for the service request data object describes a threshold-satisfying diagnosis probability for a diagnosed condition that is based at least in part on an associated a diagnosis probability, such as a high diagnosis confidence class, moderate diagnosis confidence class, and low diagnosis confidence class. In some embodiments, when a probabilistic diagnosis data object for a service request data object includes n diagnosed probabilities for n conditions, then mapping the service request data object to a diagnosis-based class comprises: (i) determining a related subset of the n diagnosed conditions that are listed as being related to the diagnosis-based class (e.g., for a contagion class, determining a related subset of the n diagnosed conditions that are listed as being non-contagious, mildly contagious, moderately contagious, and/or severely contagious), (ii) combining (e.g., summing, averaging, and/or the like) each diagnosis probability for a diagnosis condition in the related subset for the diagnosis-based class to determine a classification score for the diagnosis-based class, and (iii) mapping the service request data object to the diagnosis-based class if the classification score for the diagnosis-based class satisfies (e.g., exceeds) a classification score threshold.

A provider-based class may be an available label for a service request data object, where the service request data object may be mapped to the available label if a provider data object for the service request data object satisfies one or more conditions associated with the available label. Examples of provider-based classes include an availability class to which a service request data object is mapped if a provider schedule described by the provider data object for the service request data object includes available time slots for scheduling a service appointment associated with the service request data object.

A hybrid diagnosis class may be an available label for a service request data object, where the service request data object may be mapped to the available label if a combination of the provider data objects associated with the service request data object and the probabilistic diagnosis data object associated with the service request data object satisfies one or more conditions associated with the available label. Examples of hybrid diagnosis classes include a facility equipment class that is mapped to a service request data object if a facility is equipped with the tools and/or equipment necessary to diagnose and/or test a patient in relation to one or more diagnosed conditions described by the probabilistic diagnosis data object for the service request data object.

At step/operation 404, the predictive data analysis computing entity 106 determines the telehealth visit recommendation score for the service request data object based at least in part on the variable-length classification for the service request data object. In some embodiments, the predictive data analysis computing entity 106 combines (e.g., using a telehealth visit recommendation scoring machine learning model) each telehealth visit recommendation score for a variable-length subset of candidate classifications that are associated with the variable-length classification to generate the telehealth visit recommendation score for the service request data object. For example, consider a service request data object that is associated with a variable-length classification that describes that the service request data object is associated with candidate classifications $C_1$-$C_3$, where the candidate classifications $C_1$-$C_3$ are associated with telehealth visit recommendation scores $R_1$-$R_3$ respectively. In some embodiments, the telehealth visit recommendation score for the service request data object may be determined based at least in part on a combination of $C_1$-$C_3$ $$\left(\text{e.g., based at least in part on } \frac{C_1 + C_2 + C_3}{3}\right).$$

In some embodiments, the telehealth visit recommendation score for a candidate classification may describe a degree of correlation between mapping of the candidate classification to a service request data object and whether a telehealth visit should be scheduled with respect to the service request data object. For example, in some embodiments, the contagion class may be associated with a positive telehealth visit recommendation score, such that service request data objects having conditions associated with moderate or severe contagious probabilities may be more likely to result in a telehealth visit recommendation.

As another example, in some embodiments, the specialty class may be associated with a positive telehealth visit recommendation score, such that service request data objects having conditions associated with a specialty class other than a general specialty class may be more likely to result in a telehealth visit recommendation. For example, in an instance a service request data object indicates a requested provider, medical facility identifier, and/or the like does not have clinicians, equipment, etc. required to handle the specialty class, a positive telehealth recommendation may be determined for the patient.

As another example, in some embodiments, the diagnosis confidence class may be associated with a positive recommendation score, such that service request data objects associated with conditions with a high diagnosis probability may be more likely to result in a telehealth visit recommendation. For example, in an instance a service request data object indicates a requested provider, medical facility identifier, and/or the like which is currently limited on resources and a probabilistic data object indicates a high diagnosis probability, a positive telehealth recommendation may be determined for the patient.

As another example, in some embodiments, an availability class may be associated with a positive telehealth visit recommendation score, such that service request data objects that are associated with provider who are currently or anticipated to be unavailable are more likely to result in a telehealth visit recommendation. For example, in an instance a service request data object indicates a requested provider, medical facility identifier, and/or is currently limited on available caretakers, is experiencing long wait times, and/or the like, a positive telehealth recommendation may be determined for the patient.

As another example, in some embodiments, a facility equipment class may be associated with a positive telehealth visit recommendation score, such that service request data objects having more conditions that do not require specialized testing equipment are more likely to result in a telehealth visit recommendation.

For example, consider a scenario in which a 6-year-old girl has experienced an earache in her right ear for one day, with a current fever of 101.2 degrees Fahrenheit. Her parents use an online agent to check symptoms. Acute otitis media (i.e., an ear infection) is a possible diagnosis. Rather than driving 6 miles to the pediatrician's office, her parents may work through a client-side application and may be directed to a neighborhood telehealth facility within a mile from their home. Her parents may then use a self-service pneumatic otoscope to examine his daughter's ear with a pediatrician's direction via a peer-to-peer video telehealth session within the telehealth facility. The pediatrician may confirm the acute otitis media diagnosis and prescribe a prescription for amoxicillin, which an adjacent pharmacy may fill.

As another example, consider a scenario in which a 50-year-old woman with a history of severe asthma requiring inhaled steroids experiences loss of breath, nausea, and confusion. She may use an online agent to check her symptoms and determine that the coronavirus infection is a possible diagnosis. Given that the coronavirus is a highly contagious virus, she may be directed to a neighborhood telehealth facility and use self-service equipment and a peer-to-peer video telehealth session to confirm the diagnosis while reducing exposure to staff and other patients and additionally, reducing her own exposure to other contagions while her immune system may be weakened due to the possible infection.

In this way, various embodiments of the present invention introduce techniques for using the output of a diagnosis prediction machine learning model to generate a telehealth visit recommendation score. By using the noted techniques, various embodiments of the present invention enable using pretrained diagnosis prediction machine learning models to generate a telehealth visit recommendation score, thus reducing or avoiding the need for computationally expensive operations that are performed to generate diagnosis prediction machine learning models. In this way, various embodiments of the present invention reduce the number of computational operations performed to generate telehealth visit recommendation scores, thus improving the computational efficiency of predictive data analysis systems that are configured to generate telehealth visit recommendation scores and make important technical contributions to the field of predictive data analysis.

At step/operation 405, the predictive data analysis computing entity 106 performs one or more prediction-based actions based at least in part on the telehealth visit recommendation score. In some embodiments, performing the one or more prediction-based actions comprises, in response to determining that the telehealth visit recommendation score satisfies a telehealth visit recommendation score threshold, scheduling a telehealth visit entry on a calendar data object associated with the provider data object via interacting with an integrated calendar application programming interface (API).

In some embodiments, performing the one or more prediction-based actions comprises, in response to determining that the telehealth visit recommendation score satisfies a telehealth visit recommendation score threshold, providing a plurality of facility navigational instructions to a user device, wherein the plurality of facility navigational instructions are indicative of recommended instructions for a user to enter a particular telehealth facility. For example, the plurality of facility navigational instructions may include parking and/or drop-off instructions, entrance instructions, inter-facility navigation instructions, room assignments, room codes, and/or the like. An example of the plurality of facility navigational instructions is depicted in the exemplary user interface 700 of FIG. 7.

In some embodiments, step/operation 405 may be performed in accordance with the process that is depicted in FIG. 6. The process that is depicted in FIG. 6 begins at step/operation 601 when the predictive data analysis computing entity 106 determines, in response to determining that the telehealth visit recommendation score satisfies a telehealth visit recommendation score threshold, whether a provider associated with a provider identifier for the telehealth visit recommendation score is available for performing the telehealth visit associated with the telehealth visit recommendation score.

At step/operation 602, the predictive data analysis computing entity 106 determines, in response to determining that the provider is available for performing the telehealth associated with the telehealth visit recommendation score, whether the provider is interested in performing the telehealth visit. In some embodiments, the predictive data analysis computing entity 106 presents a prompt to the provider about confirming whether the physician is interested to perform the telehealth visit and determines the provider interest confirmation based at least in part on the provider selection of the input options provided by the prompt. An example of such a prompt is depicted in the exemplary user interface 800 of FIG. 8.

At step/operation 603, the predictive data analysis computing entity 106 schedules, in response to determining that the provider is available for performing the telehealth session associated with the telehealth visit recommendation score and that the provider is interested in performing the telehealth visit associated with the telehealth visit recommendation score, a telehealth visit with a physician is determined by the predictive data analysis computing entity 106. In some embodiments, scheduling the telehealth visit comprises scheduling a telehealth visit entry on a calendar data object associated with the available provider data object via interacting with an integrated calendar application programming interface (API). In addition to electronic integration methods, a scheduling notification can be sent to the call center for manual communication to clinical systems. In some embodiments, pager systems (e.g., secure text messaging systems) can be integrated electronically of the necessary information for telehealth visit needs (e.g., patient demographics, timing/scheduling, and additional pertinent clinical data).

At step/operation 604, the predictive data analysis computing entity 106 determines, based at least in part on a provider availability indicator describing that the provider is unavailable for performing the telehealth visit or a provider interest indicator describing that the provider is not interested in performing the telehealth visit, one or more alternative provider prompts to one or more alternative provider identifiers associated with one or more alternative providers. In some embodiments, the provider availability indicator is determined based at least in part on a response to the prompt that is generated and displayed at step/operation 601. In some embodiments, to identify an alternative provider identifier, the predictive data analysis computing entity 106: (i) identifies a set of candidate alternative provider identifiers, and (ii) for each candidate alternative provider identifier: (a) generate a service request data object that includes the diagnosis input data of the original service data object but provider data extracted from the provider data object of the candidate alternative provider identifier, (b) process the generated service request data object using the diagnosis prediction machine learning model to generate a probabilistic diagnosis data object for the candidate alternative provider identifier, (c) process the probabilistic diagnosis data object for the candidate alternative provider identifier to generate a variable-length classification for the candidate alternative provider identifier, (d) determine a telehealth visit recommendation score for the candidate alternative provider identifier based at least in part on the variable-length classification for the candidate alternative provider identifier and using a telehealth visit recommendation scoring machine learning model, a classification telehealth visit recommendation score for the candidate alternative provider identifier, and (e) identify the candidate alternative provider identifier as an alternative provider identifier if the classification telehealth visit recommendation score for the candidate alternative provider identifier satisfies a classification telehealth visit recommendation score threshold.

At step/operation 605, the predictive data analysis computing entity 106 identifies an alternative available and interested provider identifier for a telehealth visit and schedules the telehealth visit by interacting with a calendar data object for the provider identifier. In some embodiments, scheduling the telehealth visit comprises scheduling a telehealth visit on a calendar data object associated with the available provider data object via interacting with an integrated calendar application programming interface (API). In addition to electronic integration methods, a scheduling notification can be sent to the call center for manual communication to clinical systems. In some embodiments, pager systems (e.g., secure text messaging systems) can be integrated electronically of the necessary information for telehealth visit needs (e.g., patient demographics, timing/scheduling, and additional pertinent clinical data).

Accordingly, as described above, various embodiments of the present invention introduce techniques for using the output of a diagnosis prediction machine learning model to generate a telehealth visit recommendation score. By using the noted techniques, various embodiments of the present invention enable using pretrained diagnosis prediction machine learning models to generate a telehealth visit recommendation score, thus reducing or avoiding the need for computationally expensive operations that are performed to generate diagnosis prediction machine learning models. In this way, various embodiments of the present invention reduce the number of computational operations performed to generate telehealth visit recommendation scores, thus improving the computational efficiency of predictive data analysis systems that are configured to generate telehealth visit recommendation scores and make important technical contributions to the field of predictive data analysis.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A computer-implemented method comprising:
   receiving, by one or more processors, input data and a ground truth corresponding to the input data;
   inputting, by the one or more processors, the input data to a first prediction machine learning model to receive a first vector comprising a set of probabilistic values that respectively correspond to a set of conditions associated with the input data;
   inputting, by the one or more processors, the first vector to a second hybrid classification machine learning model to receive a second vector that identifies a subset of candidate classes from a plurality of candidate classes based at least in part on the set of probabilistic values of the first vector, wherein the second hybrid classification machine learning model comprises a plurality of recurrent neural networks that correspond to the plurality of candidate classes;
   inputting, by the one or more processors, the second vector to a third machine learning model to receive a score for the input data; and
   training, by the one or more processors, the first prediction machine learning model, the second hybrid classification machine learning model, and the third machine learning model end-to-end by updating one or more trainable parameters of the first prediction machine learning model, the second hybrid classification machine learning model, and the third machine learning model based at least in part on an error measure between the score and the ground truth associated with the input data.

2. The computer-implemented method of claim 1, wherein the input data comprises one or more first fields and one or more second historical fields.

3. The computer-implemented method of claim 1, wherein the plurality of candidate classes comprise a first class that is associated with: (i) a related subset of a plurality of conditions that is associated with the first class, and (ii) a classification score that is determined based at least in part on a probability for the related subset of the plurality of conditions; and the input data is mapped to the first class responsive to the classification score for the first class satisfying a classification score threshold.

4. The computer-implemented method of claim 3, wherein the first class comprises:
   a contagion class,
   specialty class, or
   a diagnosis confidence class.

5. The computer-implemented method of claim 1, wherein the plurality of candidate classes comprises a second class that comprises an availability class.

6. The computer-implemented method of claim 1, wherein the plurality of candidate classes comprises a third hybrid class that comprises a facility equipment class.

7. The computer-implemented method of claim 1, further comprising:
   providing, via an integrated calendar application programming interface (API), an event instruction for scheduling an event on a calendar data object associated with the input data.

8. The computer-implemented method of claim 1, wherein the first prediction machine learning model comprises a plurality of condition-specific machine learning components that are respectively trained to generate a respective probability for a plurality of conditions and generating the first vector comprises:

generating, using the plurality of condition-specific machine learning components, a plurality of probabilities for the plurality of conditions based at least in part on the input data;

generating a plurality of normalized probabilities by normalizing the plurality of probabilities; and generating the first vector from the plurality of normalized probabilities based at least in part on a normalized probability threshold.

9. A system comprising:

one or more processors; and at least one memory storing processor-executable instructions that, when executed by any one or more of the one or more processors, causes the one or more processors to perform operations comprising:

receiving input data and a ground truth corresponding to the input data;

inputting the input data to a first prediction machine learning model to receive a first vector comprising a set of probabilistic values that respectively correspond to a set of conditions associated with the input data;

inputting the first vector to a second hybrid classification machine learning model to receive a second vector that identifies a subset of candidate classes from a plurality of candidate classes based at least in part on the set of probabilistic values of the first vector, wherein the second hybrid classification machine learning model comprises a plurality of recurrent neural networks that correspond to the plurality of candidate classes;

inputting the second vector to a third machine learning model to receive a score for the input data; and training the first prediction machine learning model, the second hybrid classification machine learning model, and the third machine learning model end-to-end by updating one or more trainable parameters of the first prediction machine learning model, the second hybrid classification machine learning model, and the third machine learning model based at least in part on an error measure between the score and the ground truth associated with the input data.

10. The system of claim 9, wherein the input data comprises one or more first fields and one or more second historical fields.

11. The system of claim 9, wherein the plurality of candidate classes comprise a first class that is associated with: (i) a related subset of a plurality of conditions that is associated with the first class, and (ii) a classification score that is determined based at least in part on each a diagnosis probability for the related subset of the plurality of conditions; and the input data is mapped to the first class responsive to the classification score for the first class satisfying a classification score threshold.

12. The system of claim 11, wherein the first class comprises:

a contagion class,
a specialty class, or
a diagnosis confidence class.

13. The system of claim 9, wherein the plurality of candidate classes comprises a second class that comprises an availability class.

14. The system of claim 9, wherein the plurality of candidate classes comprises a third hybrid class that comprises a facility equipment class.

15. The system of claim 9, wherein the operations further comprise:

providing, via an integrated calendar application programming interface (API), an event instruction for scheduling an event on a calendar data object associated with the input data.

16. One or more non-transitory computer-readable storage media including instructions that, when executed by one or more processors, cause the one or more processors to:

receive input data and a ground truth corresponding to the input data;

input the input data to a first prediction machine learning model to receive a first vector comprising a set of probabilistic values that respectively correspond to a set of conditions associated with the input data;

input the first vector to a second hybrid classification machine learning model to receive a second vector that identifies a subset of candidate classes from a plurality of candidate classes based at least in part on the set of probabilistic values of the first vector, wherein the second hybrid classification machine learning model comprises a plurality of recurrent neural networks that correspond to the plurality of candidate classes;

input the second vector to a third machine learning model to receive a score for the input data; and train the first prediction machine learning model, the second hybrid classification machine learning model, and the third machine learning model end-to-end by updating one or more trainable parameters of the first prediction machine learning model, the second hybrid classification machine learning model, and the third machine learning model based at least in part on an error measure between the score and the ground truth associated with the input data.

17. The one or more non-transitory computer-readable storage media of claim 16, wherein the input data comprises one or more first fields and one or more second historical fields.

18. The one or more non-transitory computer-readable storage media of claim 16, wherein the plurality of candidate classes comprise a first class that is associated with: (i) a related subset of a plurality of conditions that is associated with the first class, and (ii) a classification score that is determined based at least in part on a probability for the related subset of the plurality of conditions; and the input data is mapped to the first class responsive to the classification score for the first class satisfying a classification score threshold.

* * * * *

UNITED STATES PATENT AND TRADEMARK OFFICE
CERTIFICATE OF CORRECTION

Page 1 of 1

PATENT NO. : 12,424,338 B2
APPLICATION NO. : 17/548969
DATED : September 23, 2025
INVENTOR(S) : Rick A. Hamilton et al.

It is certified that error appears in the above-identified patent and that said Letters Patent is hereby corrected as shown below:

In the Claims

In Column 28, Claim 4, Line 52, delete "specialty" and insert -- a specialty --, therefor.

In Column 29, Claim 11, Line 52, delete "each a diagnosis" and insert -- a --, therefor.

Signed and Sealed this
Tenth Day of February, 2026

John A. Squires
*Director of the United States Patent and Trademark Office*